US011737743B2

(12) United States Patent
Fatone et al.

(10) Patent No.: US 11,737,743 B2
(45) Date of Patent: *Aug. 29, 2023

(54) DILATION SYSTEM AND METHOD OF USING THE SAME

(71) Applicant: DePuy Synthes Products, Inc., Raynham, MA (US)

(72) Inventors: Peter Fatone, Exton, PA (US); Brandon Randall, Chester Springs, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 212 days.

This patent is subject to a terminal disclaimer.

(21) Appl. No.: 17/181,477

(22) Filed: Feb. 22, 2021

(65) Prior Publication Data

US 2021/0169461 A1 Jun. 10, 2021

Related U.S. Application Data

(63) Continuation of application No. 16/266,191, filed on Feb. 4, 2019, now Pat. No. 10,925,594, which is a continuation of application No. 15/964,561, filed on Apr. 27, 2018, now Pat. No. 10,194,895, which is a continuation of application No. 15/680,433, filed on Aug. 18, 2017, now Pat. No. 9,974,533, which is a (Continued)

(51) Int. Cl.
*A61B 17/34* (2006.01)
*A61B 17/02* (2006.01)
(Continued)

(52) U.S. Cl.
CPC .......... *A61B 17/025* (2013.01); *A61B 5/296* (2021.01); *A61B 5/4893* (2013.01);
(Continued)

(58) Field of Classification Search
CPC .............. A61B 17/025; A61B 17/1757; A61B 17/3417; A61B 17/3421; A61B 2017/3433; A61F 2/4611
See application file for complete search history.

(56) References Cited

U.S. PATENT DOCUMENTS 2,878,701 A 3/1959 Weersma
3,698,391 A 10/1972 Mahony
(Continued)

FOREIGN PATENT DOCUMENTS

CN 102727309 A 10/2012
DE 9415039 U1 11/1994
(Continued)

OTHER PUBLICATIONS

International Search Report and Written Opinion (PCT/US08/78927) dated Jan. 14, 2009.
(Continued)

*Primary Examiner* — Diane D Yabut
(74) *Attorney, Agent, or Firm* — Dunlap Codding, P.C.

(57) ABSTRACT

A method of forming an access opening through a psoas muscle to a patient's spine includes laterally inserting a stimulating dilator into the psoas muscle. The stimulating dilator has a stimulation channel formed in an outer surface thereof. An electrical pulse is transmitted into the stimulating dilator to locate a position of a nerve in the patient's psoas muscle. The stimulating dilator is laterally inserted through the psoas muscle and toward the patient's spine in a way that avoids the nerve. A stimulating probe is inserted into the stimulation channel along the outer surface of the stimulating dilator while transmitting an electrical pulse into the stimulating probe to verify the position of the nerve.

16 Claims, 6 Drawing Sheets

Related U.S. Application Data continuation of application No. 15/202,738, filed on Jul. 6, 2016, now Pat. No. 9,737,290, which is a continuation of application No. 12/681,671, filed as application No. PCT/US2008/078927 on Oct. 6, 2008, now Pat. No. 9,387,009.

(60) Provisional application No. 60/977,882, filed on Oct. 5, 2007.

(51) Int. Cl.
| | |
|---|---|
| *A61B 5/296* | (2021.01) |
| *A61B 5/00* | (2006.01) |
| A61B 17/17 | (2006.01) |
| A61F 2/46 | (2006.01) |
| A61B 17/00 | (2006.01) |
| A61B 90/00 | (2016.01) |

(52) U.S. Cl.
CPC ...... *A61B 17/0218* (2013.01); *A61B 17/3421* (2013.01); *A61B 17/3423* (2013.01); *A61B 17/1757* (2013.01); *A61B 17/3417* (2013.01); *A61B 17/3476* (2013.01); *A61B 2017/003* (2013.01); *A61B 2017/00039* (2013.01); *A61B 2017/00331* (2013.01); *A61B 2017/0262* (2013.01); *A61B 2017/3433* (2013.01); *A61B 2090/062* (2016.02); *A61F 2/4611* (2013.01)

(56) References Cited

U.S. PATENT DOCUMENTS

| | | |
|---|---|---|
| 4,350,151 A | 9/1982 | Scott |
| 4,449,532 A | 5/1984 | Storz |
| 4,573,448 A | 3/1986 | Kambin |
| 4,646,738 A | 3/1987 | Trott |
| 4,678,459 A | 7/1987 | Onik et al. |
| 4,716,901 A | 1/1988 | Jackson et al. |
| 4,862,891 A | 9/1989 | Smith |
| 4,863,430 A | 9/1989 | Klyce et al. |
| 4,888,146 A | 12/1989 | Dandeneau |
| 5,071,410 A | 12/1991 | Pazell |
| 5,080,662 A | 1/1992 | Paul |
| 5,120,318 A | 6/1992 | Nallapareddy |
| 5,129,906 A | 7/1992 | Ross et al. |
| 5,152,765 A | 10/1992 | Ross et al. |
| 5,158,543 A | 10/1992 | Lazarus |
| 5,171,279 A | 12/1992 | Mathews |
| 5,195,541 A | 3/1993 | Obenchain |
| 5,241,972 A | 9/1993 | Bonati |
| 5,242,443 A | 9/1993 | Kambin |
| 5,285,795 A | 2/1994 | Ryan et al. |
| 5,357,983 A | 10/1994 | Mathews |
| 5,395,317 A | 3/1995 | Kambin |
| 5,439,464 A | 8/1995 | Shapiro |
| 5,472,426 A | 12/1995 | Bonati et al. |
| 5,480,440 A | 1/1996 | Kambin |
| 5,496,322 A | 3/1996 | Mathews |
| 5,520,609 A | 5/1996 | Moll et al. |
| 5,529,580 A | 6/1996 | Kusunoki et al. |
| 5,540,706 A | 7/1996 | Aust et al. |
| 5,545,228 A | 8/1996 | Kambin |
| 5,569,248 A | 10/1996 | Mathews |
| 5,569,290 A | 10/1996 | McAfee |
| 5,575,176 A | 11/1996 | Rohrs et al. |
| 5,580,344 A | 12/1996 | Hasson |
| 5,584,887 A | 12/1996 | Kambin |
| 5,591,187 A | 1/1997 | Dekel |
| 5,601,569 A | 2/1997 | Pisharodi |
| 5,662,300 A | 9/1997 | Michelson |
| 5,688,222 A | 11/1997 | Hluchy et al. |
| 5,728,097 A | 3/1998 | Mathews |
| 5,730,754 A | 3/1998 | Obenchain |
| 5,733,242 A | 3/1998 | Rayburn et al. |
| 5,735,792 A | 4/1998 | Vanden Hoek et al. |
| 5,741,261 A | 4/1998 | Moskovitz et al. |
| 5,762,629 A | 6/1998 | Kambin |
| 5,792,044 A | 8/1998 | Foley et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,902,231 A | 5/1999 | Foley et al. |
| 5,910,155 A | 6/1999 | Ratcliff et al. |
| 5,954,635 A | 9/1999 | Foley et al. |
| 5,964,698 A | 10/1999 | Fowler |
| 5,964,761 A | 10/1999 | Kambin |
| 5,967,970 A | 10/1999 | Cowan et al. |
| 5,976,146 A | 11/1999 | Ogawa et al. |
| 6,033,105 A | 3/2000 | Barker et al. |
| 6,053,907 A | 4/2000 | Zirps |
| 6,063,021 A | 5/2000 | Hossain et al. |
| 6,099,547 A | 8/2000 | Gellman et al. |
| 6,110,182 A | 8/2000 | Mowlai-Ashtiani |
| 6,152,871 A | 11/2000 | Foley et al. |
| 6,159,179 A | 12/2000 | Simonson |
| 6,162,170 A | 12/2000 | Foley et al. |
| 6,175,758 B1 | 1/2001 | Kambin |
| 6,200,322 B1 | 3/2001 | Branch et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,336,914 B1 | 1/2002 | Gillespie, III |
| 6,354,992 B1 | 3/2002 | Kato |
| 6,360,750 B1 | 3/2002 | Gerber et al. |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,520,907 B1 | 2/2003 | Foley et al. |
| 6,558,407 B1 | 5/2003 | Ivando et al. |
| 6,575,899 B1 | 6/2003 | Foley et al. |
| 6,575,979 B1 | 6/2003 | Cragg |
| 6,575,987 B2 | 6/2003 | Gellman et al. |
| 6,579,281 B2 | 6/2003 | Palmer et al. |
| 6,589,225 B2 | 7/2003 | Orth et al. |
| 6,589,262 B1 | 7/2003 | Honebrink et al. |
| 6,626,830 B1 | 9/2003 | Califiore et al. |
| 6,637,435 B2 | 10/2003 | Ciaglia et al. |
| 6,648,915 B2 | 11/2003 | Sazy |
| 6,676,597 B2 | 1/2004 | Guenst et al. |
| 6,679,833 B2 | 1/2004 | Smith et al. |
| 6,688,564 B2 | 2/2004 | Salvermoser et al. |
| 6,709,389 B2 | 3/2004 | Farascioni |
| 6,758,809 B2 | 7/2004 | Briscoe et al. |
| 6,793,656 B1 | 9/2004 | Mathews |
| 6,808,505 B2 | 10/2004 | Kadan |
| 6,887,198 B2 | 5/2005 | Phillips et al. |
| 6,932,765 B2 | 8/2005 | Berg |
| 6,983,930 B1 | 1/2006 | La Mendola et al. |
| 7,008,431 B2 | 3/2006 | Simonson |
| 7,079,883 B2 | 7/2006 | Marino et al. |
| 7,087,058 B2 | 8/2006 | Cragg |
| 7,104,986 B2 | 9/2006 | Hovda et al. |
| 7,108,698 B2 | 9/2006 | Robbins et al. |
| 7,137,949 B2 | 11/2006 | Scirica et al. |
| 7,182,731 B2 | 2/2007 | Nguyen et al. |
| 7,226,413 B2 | 6/2007 | McKinley |
| 7,305,989 B2 | 12/2007 | Gostelow |
| 7,341,556 B2 | 3/2008 | Shalman |
| 7,434,325 B2 | 10/2008 | Foley et al. |
| 7,435,219 B2 | 10/2008 | Kim |
| 7,582,058 B1 | 9/2009 | Miles et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,691,057 B2 | 4/2010 | Miles et al. |
| 7,771,384 B2 | 8/2010 | Ravo |

(56) References Cited

U.S. PATENT DOCUMENTS

| | | |
|---|---|---|
| 7,785,253 B1 | 8/2010 | Arambula et al. |
| 7,794,456 B2 | 9/2010 | Sharps et al. |
| 7,811,303 B2 | 10/2010 | Fallin et al. |
| 7,931,579 B2 | 4/2011 | Bertolero et al. |
| 7,935,051 B2 | 5/2011 | Miles et al. |
| 7,946,981 B1 | 5/2011 | Cubb |
| 7,951,141 B2 | 5/2011 | Sharps et al. |
| 7,959,564 B2 | 6/2011 | Ritland |
| RE42,525 E | 7/2011 | Simonson |
| 7,988,623 B2 | 8/2011 | Pagliuca et al. |
| 8,005,535 B2 | 8/2011 | Gharib et al. |
| 8,007,492 B2 | 8/2011 | DiPoto et al. |
| 8,027,716 B2 | 9/2011 | Gharib et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,092,464 B2 | 1/2012 | McKay |
| 8,096,944 B2 | 1/2012 | Harrel |
| 8,114,019 B2 | 2/2012 | Miles et al. |
| 8,202,216 B2 | 6/2012 | Melkent et al. |
| 8,236,006 B2 | 8/2012 | Hamada |
| 8,262,571 B2 | 9/2012 | Ritland |
| 8,313,430 B1 | 11/2012 | Pimenta |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,617,062 B2 | 12/2013 | Mire et al. |
| 8,622,894 B2 | 1/2014 | Banik et al. |
| 8,636,655 B1 | 1/2014 | Childs |
| 8,690,764 B2 | 4/2014 | Clark et al. |
| 8,702,600 B2 | 4/2014 | Perrow |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,605 B2 | 1/2015 | Greenberg |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,490 B2 | 2/2016 | Bowman et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,009 B2 | 7/2016 | Fatone et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 9,888,911 B2 | 2/2018 | Siegal |
| 2002/0022762 A1 | 2/2002 | Beane et al. |
| 2002/0035373 A1 | 3/2002 | Carlson et al. |
| 2002/0138020 A1 | 9/2002 | Pflueger |
| 2003/0083555 A1 | 5/2003 | Hunt et al. |
| 2003/0083688 A1 | 5/2003 | Simonson |
| 2003/0171744 A1 | 9/2003 | Leung et al. |
| 2003/0191474 A1 | 10/2003 | Cragg et al. |
| 2003/0195405 A1 | 10/2003 | Marino et al. |
| 2004/0059339 A1 | 3/2004 | Roehm, III et al. |
| 2004/0093001 A1 | 5/2004 | Hamada |
| 2004/0122446 A1 | 6/2004 | Solar |
| 2004/0127992 A1 | 7/2004 | Serhan et al. |
| 2004/0138662 A1 | 7/2004 | Landry et al. |
| 2004/0143165 A1 | 7/2004 | Alleyne |
| 2004/0147928 A1 | 7/2004 | Landry et al. |
| 2004/0172022 A1 | 9/2004 | Landry et al. |
| 2004/0225196 A1 | 11/2004 | Ruane |
| 2005/0085692 A1 | 4/2005 | Kiehn et al. |
| 2005/0090848 A1 | 4/2005 | Adams |
| 2005/0149035 A1 | 7/2005 | Pimenta et al. |
| 2005/0187570 A1 | 8/2005 | Nguyen et al. |
| 2005/0256525 A1 | 11/2005 | Culbert et al. |
| 2006/0004398 A1 | 1/2006 | Binder, Jr. et al. |
| 2006/0106416 A1 | 5/2006 | Raymond et al. |
| 2006/0195017 A1 | 8/2006 | Shluzas et al. |
| 2006/0217754 A1 | 9/2006 | Boehm, Jr. et al. |
| 2006/0247651 A1 | 11/2006 | Roehm, III et al. |
| 2007/0055259 A1 | 3/2007 | Norton et al. |
| 2007/0066977 A1 | 3/2007 | Assell et al. |
| 2007/0073110 A1 | 3/2007 | Larson et al. |
| 2007/0073111 A1 | 3/2007 | Bass |
| 2007/0100212 A1 | 5/2007 | Pimenta et al. |
| 2007/0129634 A1 | 6/2007 | Hickey et al. |
| 2007/0149975 A1 | 6/2007 | Oliver et al. |
| 2007/0156024 A1 | 7/2007 | Frasier et al. |
| 2007/0198062 A1 | 8/2007 | Miles et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2007/0282171 A1 | 12/2007 | Karpowicz et al. |
| 2008/0003325 A1 | 1/2008 | Seaver |
| 2008/0015621 A1 | 1/2008 | Emanuel |
| 2008/0021284 A1 | 1/2008 | Hestad et al. |
| 2008/0033251 A1 | 2/2008 | Araghi |
| 2008/0058606 A1 | 3/2008 | Miles et al. |
| 2008/0081951 A1 | 4/2008 | Frasier et al. |
| 2008/0188714 A1 | 8/2008 | McCaffrey |
| 2008/0215081 A1 | 9/2008 | Hsueh et al. |
| 2008/0319290 A1 | 12/2008 | Mao et al. |
| 2009/0018566 A1 | 1/2009 | Escudero et al. |
| 2009/0062871 A1 | 3/2009 | Chin et al. |
| 2009/0105543 A1 | 4/2009 | Miller et al. |

(56) References Cited

U.S. PATENT DOCUMENTS

| | | |
|---|---|---|
| 2009/0124860 A1 | 5/2009 | Miles et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0259107 A1 | 10/2009 | Crenshaw et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0022845 A1 | 1/2010 | Ott et al. |
| 2010/0076476 A1 | 3/2010 | To et al. |
| 2010/0076502 A1 | 3/2010 | Guyer et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0222644 A1 | 9/2010 | Sebastian et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2010/0317989 A1 | 12/2010 | Gharib et al. |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0230782 A1 | 9/2011 | Bartol et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0245431 A1 | 9/2012 | Baudouin et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0261401 A1 | 10/2013 | Hawkins et al. |
| 2013/0274557 A1 | 10/2013 | Bowman et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0066940 A1 | 3/2014 | Fang et al. |
| 2014/0074170 A1 | 3/2014 | Mertens et al. |
| 2014/0088367 A1 | 3/2014 | DiMauro et al. |
| 2014/0128682 A1 | 5/2014 | Loebl et al. |
| 2014/0135584 A1 | 5/2014 | Lee et al. |
| 2014/0142584 A1 | 5/2014 | Sweeney |
| 2014/0148647 A1 | 5/2014 | Okazaki |
| 2014/0172002 A1 | 6/2014 | Predick |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257035 A1 | 9/2014 | Blain |
| 2014/0257489 A1 | 9/2014 | Warren et al. |
| 2014/0275799 A1 | 9/2014 | Schuele |
| 2014/0275800 A1 | 9/2014 | Miles et al. |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0051448 A1 | 2/2015 | Hunt et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0271513 A1 | 9/2018 | Perrow et al. |

FOREIGN PATENT DOCUMENTS

| | | |
|---|---|---|
| DE | 29916026 U1 | 12/1999 |
| EP | 0537116 A1 | 4/1993 |
| EP | 0792620 A2 | 9/1997 |
| EP | 0807415 A2 | 11/1997 |
| EP | 1 340 467 | 9/2003 |
| EP | 2179695 A2 | 4/2010 |
| GB | 2481727 B | 1/2012 |
| JP | 2003169809 A | 6/2003 |
| WO | 1996/029014 | 9/1996 |
| WO | 2001/056490 | 8/2001 |
| WO | 2001/089371 | 11/2001 |
| WO | 2002/002016 | 1/2002 |
| WO | 2004/091426 | 10/2004 |
| WO | 2004/103430 | 12/2004 |
| WO | 2005/094695 | 10/2005 |
| WO | 2005/096735 | 10/2005 |
| WO | 2007/016368 | 2/2007 |
| WO | 2007/087536 | 8/2007 |
| WO | 2008/121162 | 10/2008 |
| WO | 2009/033207 | 3/2009 |
| WO | 2011/069036 | 6/2011 |
| WO | 2011/112878 | 9/2011 |
| WO | 2013/033426 | 3/2013 |
| WO | 2013/059640 | 4/2013 |
| WO | 2014/050236 | 4/2014 |
| WO | 2014/100761 | 6/2014 |
| WO | 2014/185334 | 11/2014 |
| WO | 2016/111373 | 7/2016 |
| WO | 2016/131077 | 8/2016 |
| WO | 2016/168673 | 10/2016 |
| WO | 2017/006684 | 1/2017 |
| WO | 2017/015480 | 1/2017 |
| WO | 2017/083648 | 5/2017 |

OTHER PUBLICATIONS

Adam Schriber, M.D., "Does Percutaneous Nucleotomy With Discoscopy Replace Conventional Discectomy?" Clinical Orthopedics and Related Research (1989).

Adam Schrieber, M.D., "Percutaneous Nucleotomy: Technique with Discoscopy," Orthopedics (1991).

(56) References Cited

OTHER PUBLICATIONS

Hallett H. Matthews, M.D., "Percutaneous Interbody Fusions," Spinal Fusion (1998).
Takatomo Moro, M.D. et al., "An Anatomic Study of the Lumbar Plexis with Respect to Retroperitoneal Endoscopic Surgery," SPINE (28.5) pp. 423-428 (2003).
Partial European Search Report (EP13163266.3-1654); dated Jul. 12, 2013; 8 pages.
Extended European Search Report (EP13163266.3-1654); dated Oct. 30, 2013; 13 pages.
Invitation to pay fees (PCT/US16/50022), dated Nov. 3, 2016, 2 pages.
Percutaneous Transforaminal Endoscopic Disectomy: The Thessys Method; Menno Iprenburg; 17 pgs.
International Search Report and Written Opinion (PCT/US2015/043554) dated Nov. 19, 2015: 8 pgs.
International Search Report and Written Opinion (PCT/US2015/048485) dated Feb. 9, 2016; 16 pgs.
Invitation to Pay Fees (PCT/US2016/050022); dated Nov. 3, 2016; 2 pgs.
International Search Report and Written Opinion (PCT/US2015/060978) dated Feb. 15, 2016; 8 pgs.
International Search Report and Written Opinion (PCT/US2016/050022) dated Feb. 1, 2017; 19 pgs.
A hands-free region-of-interest selection interface for solo surgery with a wide-angle endoscope: preclinical proof of concept; Kyunghwa Jung; Published online Aug. 8, 2016; 7 pgs.
Maxcess XLIF Surgical Technique; Oct. 16, 2012; 30 pgs.
Mechanomyography is more sensitive than EMG in detecting age-related sarcopenia; Journal of Biomechanics; vol. 43, Issue 3; Feb. 10, 2010; pp. 551-556; 20 pgs.
Iprenburg, M, "Percutaneous Transforaminal Endoscopic Discectomy: The Thessys Method," in Lewandrowski, K., et al., Minimally Invasive Spinal Fusion Techniques, Summit Communications, 2008 pp. 65-81.

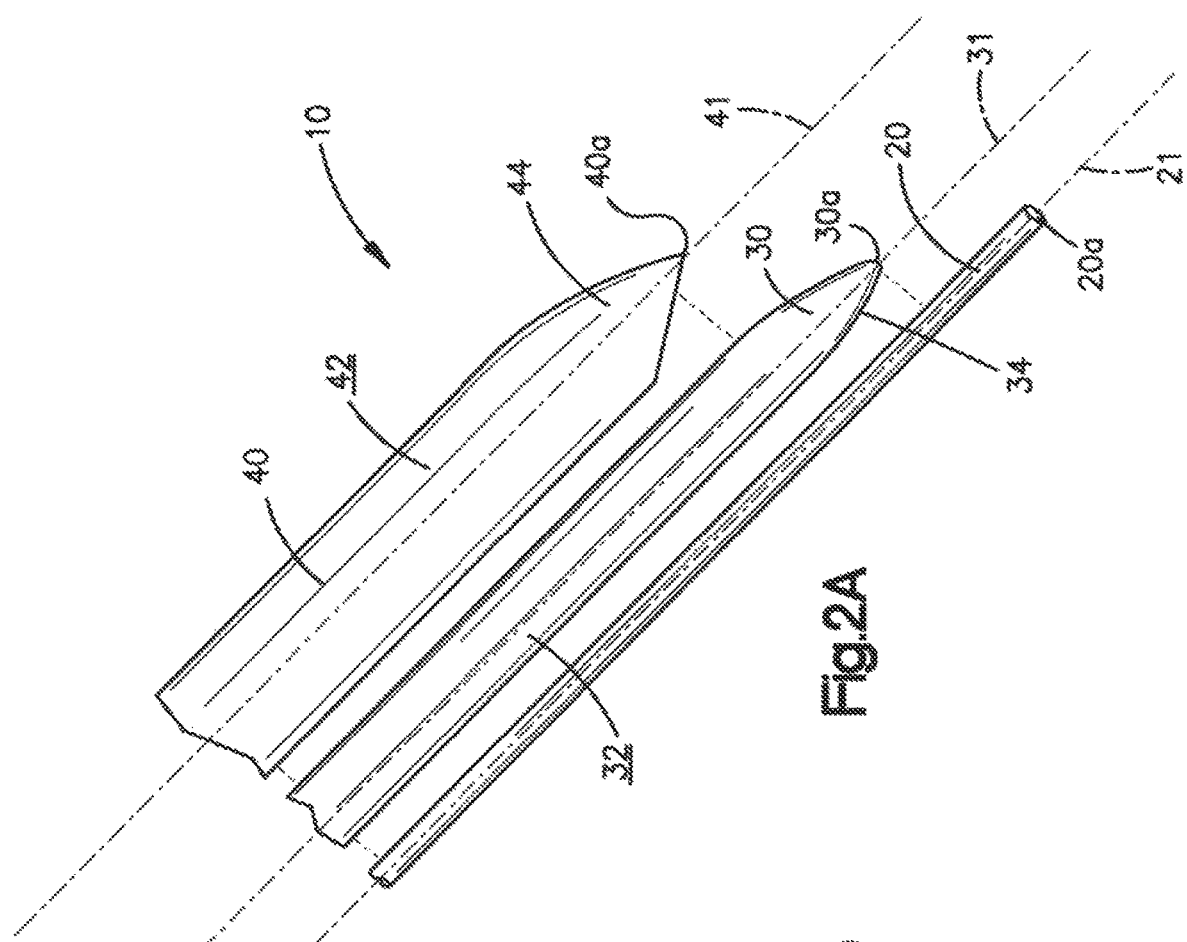
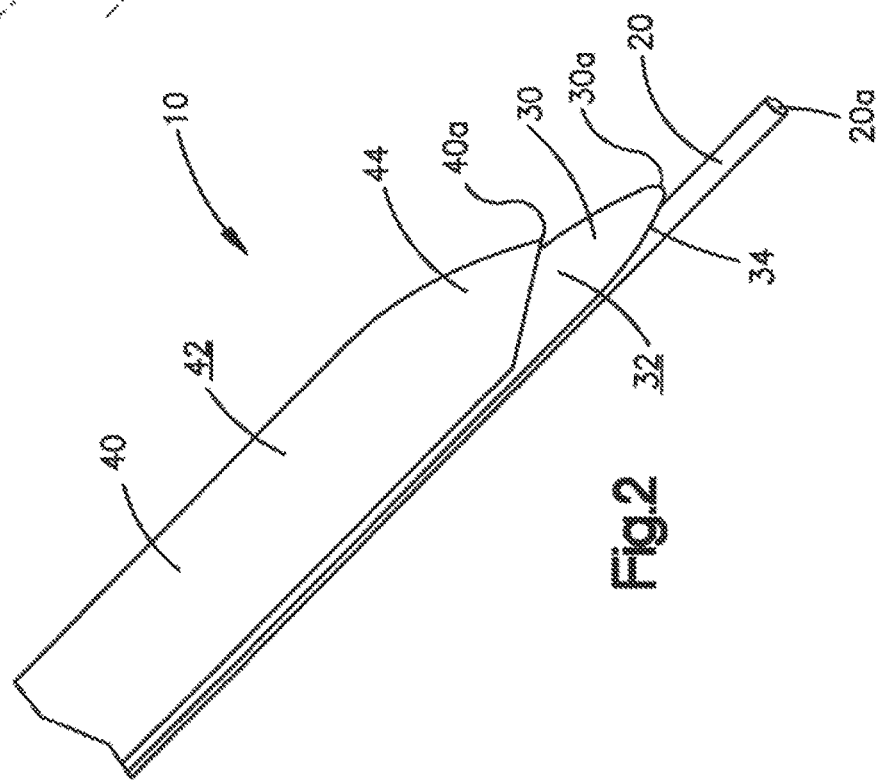

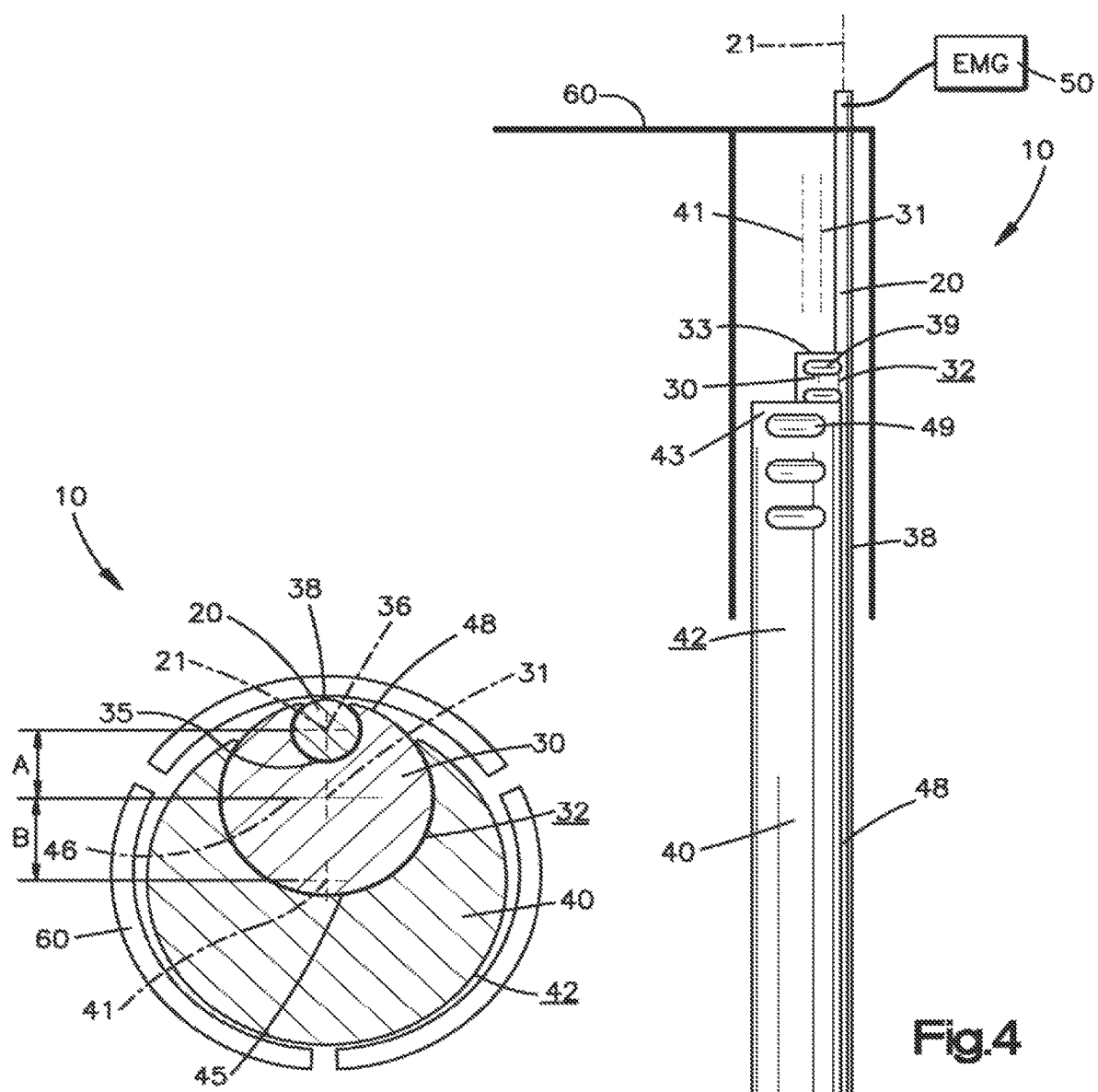
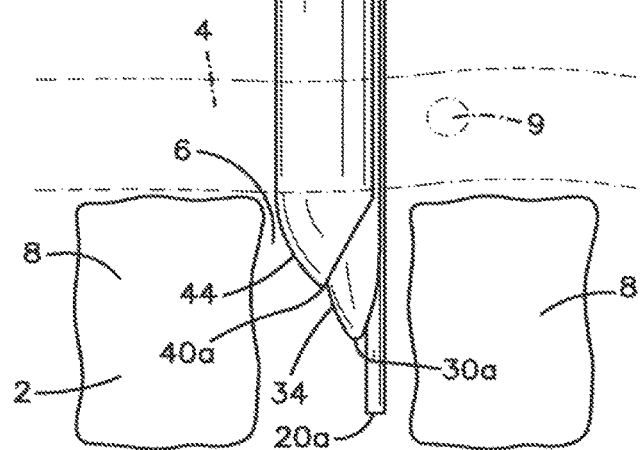

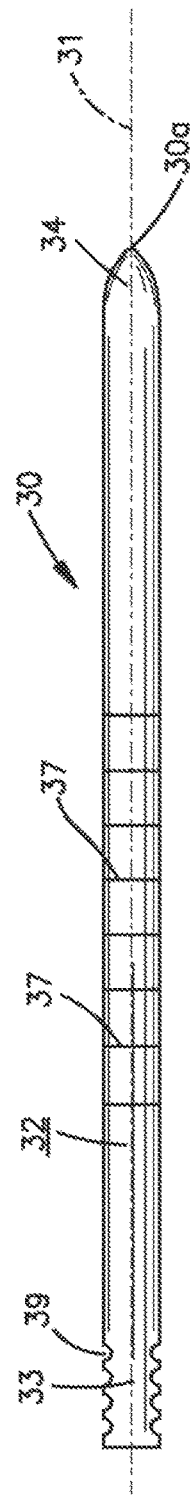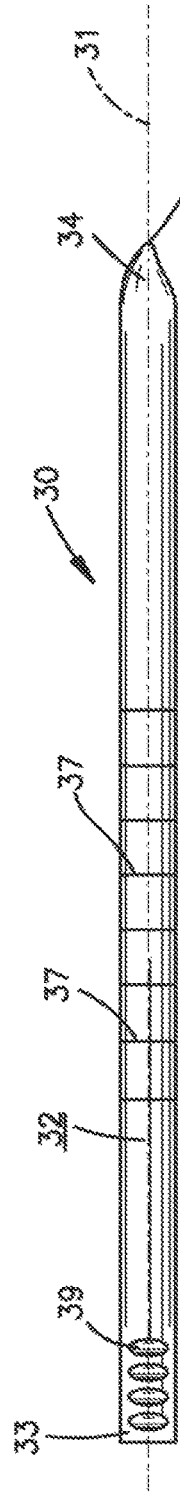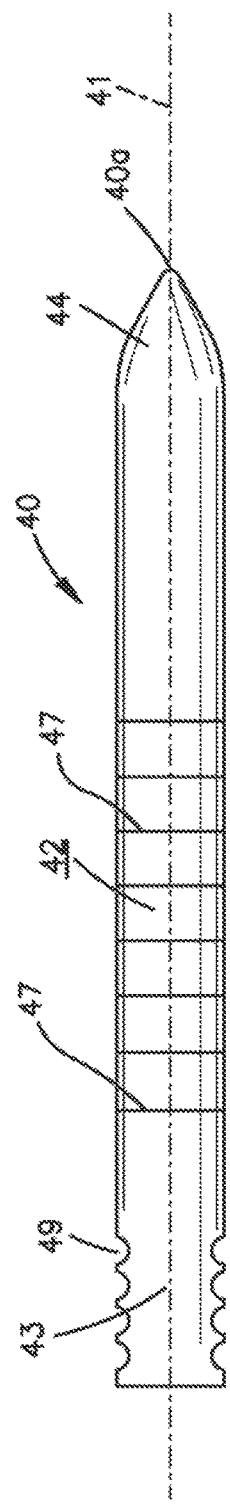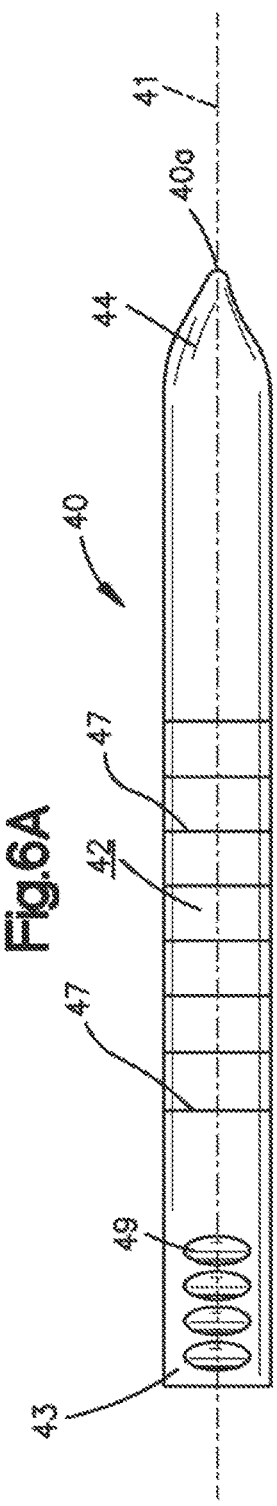

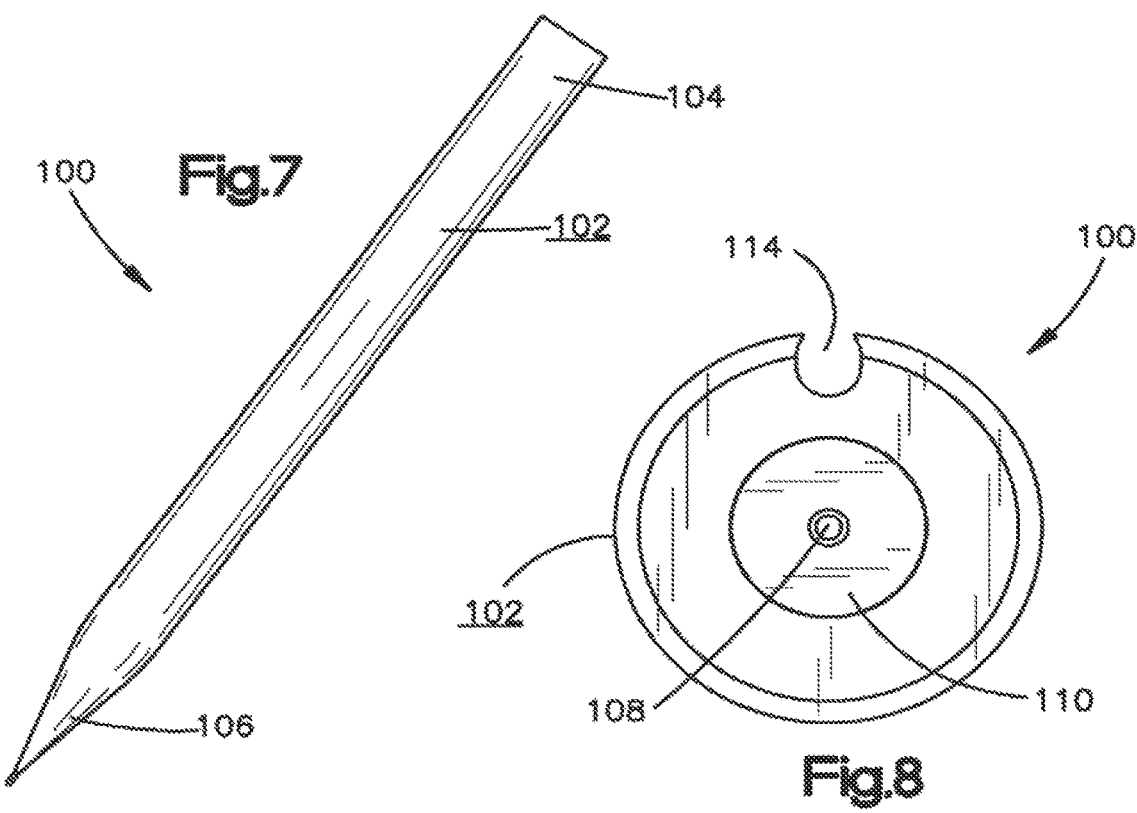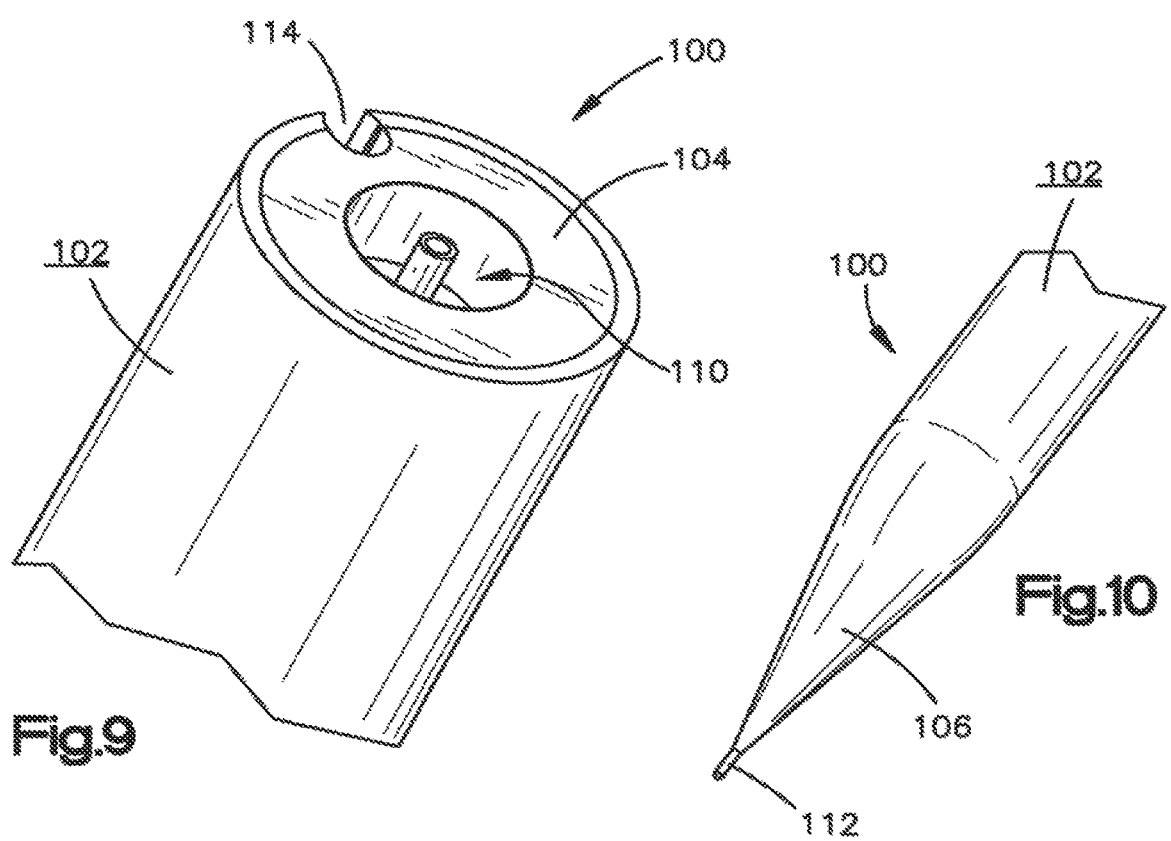

DILATION SYSTEM AND METHOD OF USING THE SAME

CROSS-REFERENCE TO RELATED APPLICATIONS

This application is a continuation of U.S. patent application Ser. No. 16/266,191, filed on Feb. 4, 2019; which is a continuation of U.S. patent application Ser. No. 15/964,561, filed on Apr. 27, 2018, now U.S. Pat. No. 10,194,895; which is a continuation of U.S. patent application Ser. No. 15/680,433, filed on Aug. 18, 2017, now U.S. Pat. No. 9,974,533; which is a continuation of U.S. patent application Ser. No. 15/202,738, filed on Jul. 6, 2016, now U.S. Pat. No. 9,737,290; which is a continuation of U.S. patent application Ser. No. 12/681,671, filed on Apr. 5, 2010, now U.S. Pat. No. 9,387,009, issued on Jul. 12, 2016; which is a U.S. National Stage Entry of PCT/US08/78927, filed on Oct. 6, 2008; which claims the benefit of U.S. Provisional Application No. 60/977,882, filed on Oct. 5, 2007, entitled "ADJACENT OR LATERAL DILATOR AND METHOD OF USING THE SAME;" the entire contents of each being hereby expressly incorporated by reference herein.

BACKGROUND OF THE INVENTION

Generally speaking, sequential dilation systems enable a surgeon to make an initial incision and gradually increase the size of the incision by sequential insertion of increasingly larger dilators. Sequential dilation is preferably able to reduce tissue damage and associated trauma to speed patient recovery time. In addition, dilation is utilized to prepare a surgical path to a surgical site and a stimulator may be utilized with the dilator to direct the dilator along a path that avoids specific areas of the patient's anatomy, such as neural elements or nerves.

SUMMARY OF THE INVENTION

A preferred embodiment of the present invention relates generally to minimally invasive surgical procedures and apparatus and, more particularly, to a dilation system and related methods for directional dilation of an incision for use in creating an access opening to a patient's spine. More specifically, the present invention relates to a dilation system and related methods that are able to laterally access a lumbar region of a patient's spine through the patient's psoas muscle. In accordance with one aspect of the present invention, the neural elements or nerves of the psoas muscle are preferably mapped using a stimulating probe, thereby defining a safe zone of passage. The stimulating probe is inserted through the psoas muscle and toward or into the intervertebral disc space. Directional dilators may be used to dilate the psoas muscle to substantially separate tissue on only one side of the stimulating probe. That is, directional, sequential dilators may be inserted to dilate the psoas muscle, for example, on the anterior side of the stimulating probe while substantially leaving the psoas muscle intact on the posterior side of the stimulating probe. Specifically, the directional, sequential dilators may be utilized to directionally dilate tissue away from a neural element or nerve in the patient's body that is identified by the stimulating probe such that the neural element or nerve is not disturbed or damaged by the dilation process or other surgical procedures that may occur following dilation.

Alternatively, the dilation system and method may include a blunt stimulating dilator including at least one channel formed in an outer surface. The channel receives a stimulating probe that is used to map the neural elements or nerves of the psoas muscle and define a safe zone of passage to the patient's spine. The stimulating dilator is inserted through the psoas muscle and toward or into the intervertebral disc space. A stimulating probe is then inserted into the channel formed in the outer surface of the stimulating dilator in order to verify the neural elements or nerves.

BRIEF DESCRIPTION OF THE DRAWINGS

The foregoing summary, as well as the following detailed description of the preferred embodiments of the application, will be better understood when read in conjunction with the appended drawings. For the purposes of illustrating the dilation system and methods of the present application, there is shown in the drawings preferred embodiments. It should be understood, however, that the application is not limited to the precise arrangements and instrumentalities shown. In the drawings:

FIG. 2 illustrates a magnified perspective view of the distal end of the directional sequential dilation system shown in FIG. 1;

FIG. 2A illustrates an exploded view of the distal end of the directional sequential dilation system shown in FIG. 2;

FIG. 3 illustrates a cross-sectional view of the directional sequential dilation system of FIG. 1, taken along line 3-3 of FIG. 1;

FIG. 4 illustrates a front elevational view of the directional sequential dilation system shown in FIG. 1 including a schematic representation of a retractor that may be used in connection with the directional sequential dilation system;

FIG. 5A illustrates a side view of a first directional dilator used in connection with the directional sequential dilation system shown in FIG. 1;

FIG. 5B illustrates a front view of the first directional dilator shown in FIG. 5A;

FIG. 6A illustrates a side view of a second directional dilator used in connection with the directional sequential dilation system shown in FIG. 1;

FIG. 6B illustrates a front view of the second directional dilator shown in FIG. 6A;

FIG. 7 illustrates a side elevational view of a dilation system in accordance with a second preferred embodiment of the present invention, which will generally be referred to herein as a blunt stimulating dilation system;

FIG. 8 illustrates a top plan view of the blunt stimulating dilation system of FIG. 7;

FIG. 9 illustrates a magnified, top perspective view of a proximal end of the blunt stimulating dilation system of FIG. 7;

FIG. 10 illustrates a magnified bottom perspective view of a distal end of the blunt stimulating dilation system of FIG. 7;

DETAILED DESCRIPTION OF THE INVENTION

Figure 1:
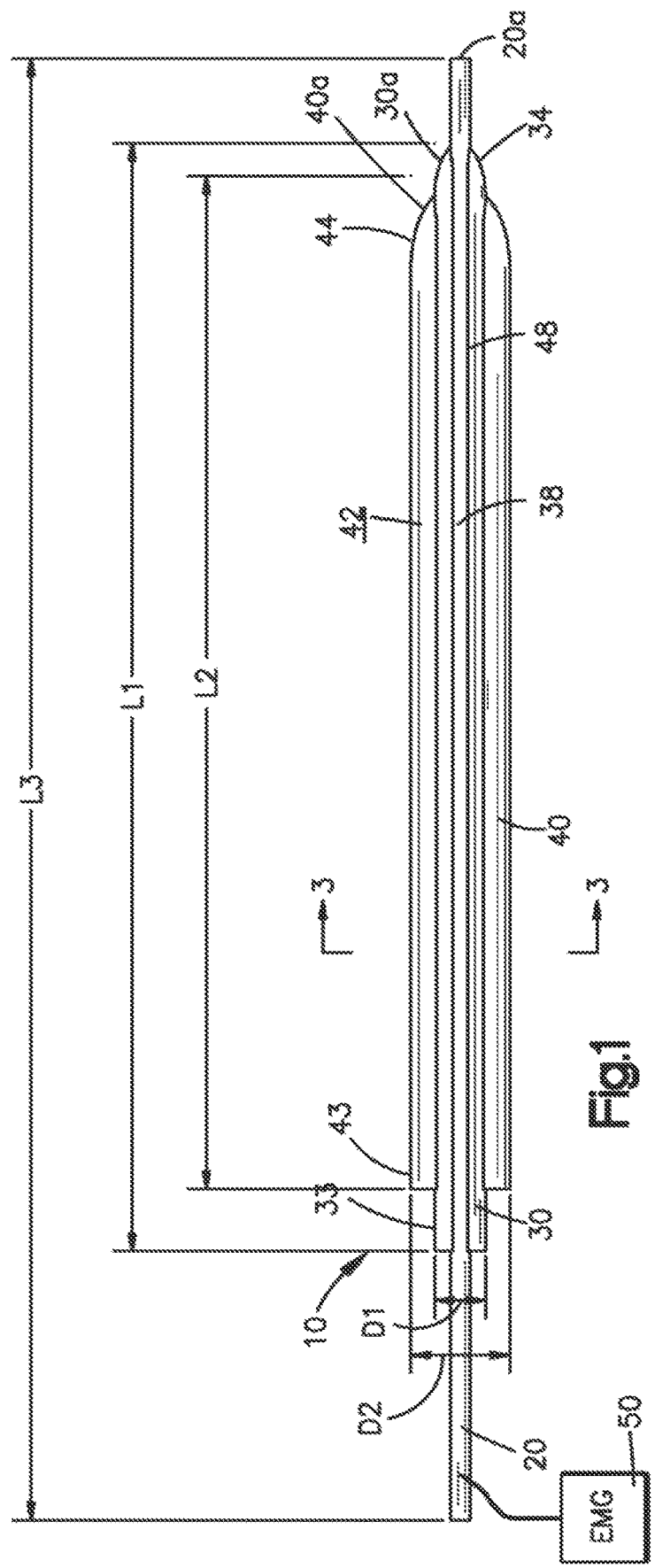
FIG. 1 illustrates a side elevational view of a dilation system in accordance with a first preferred embodiment the present invention, which will generally be referred to herein as a directional sequential dilation system.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the directional sequential and blunt stimulating dilation systems and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to dilation systems for accessing a patient's spinal column and, preferably, for laterally accessing the lumbar region of the patient's spine.

As generally understood by one of ordinary skill in the art, the dilation systems will be described in connection with accessing the spine to perform a surgical procedure, but the dilation systems will find use not only in orthopedic surgery, but in other surgical procedures in which a surgeon wishes to gain access to an internal cavity by cutting the skin and going through the body wall in order to keep the incision spread apart so that surgical instruments can be inserted. For example, the dilation systems may be used for anteriorly or posteriorly accessing the spine, for accessing the thoracic or cervical region of the spine, or for accessing nearly any other part of the body.

Referring to FIG. 4, generally speaking, during a lateral approach to a patient's spine 2, a psoas muscle 4, which is located on either side of the spine 2, is preferably separated in order to access the spine 2 and, in particular, an intervertebral disc space 6 or one or more vertebral bodies 8 within a patient's spinal column. It is desirable to avoid neural elements or nerves 9 of the lumbar plexus that lie within the psoas muscle 4 during such procedures. The anterior third of the psoas muscle 4 is typically considered a safe zone for muscle separation.

The neural elements or nerves 9 of the psoas muscle 4 are preferably mapped using a stimulating probe 20. In this manner, the most posterior neural or nerve free area of the psoas muscle 4 is preferably located and identified. The stimulating probe 20 may then be inserted through the psoas muscle 4 via the most posterior neural or nerve free tissue area or through nearly any other region that is free of neural elements or nerves 9 and toward the spine 2 or into the intervertebral disc space 6 in order to initiate safe tissue separation of the psoas muscle 4. Directional dilators 30, 40 in accordance with the first preferred embodiment of the present invention may be used to dilate the muscle separation. In particular, the directional dilators 30, 40 may be used to primarily separate tissue on one side of the stimulating probe 20 (shown as cranial side), preferably on the anterior side of the stimulating probe 20 (e.g., the safe zone as initially identified and marked by the stimulating probe 20). That is, by using the directional sequential dilators 30, 40, the tissue on one side of the stimulating probe 20 may be moved while substantially limiting movement of the tissue on the opposite side of the stimulating probe 20. In comparison, concentric dilators separate the muscle radially and, as such, dilate tissue on both sides of the stimulating probe. This in turn may impinge on neural elements or nerves 9 located outside of the safe zone.

Referring to FIGS. 1-6B, a first preferred embodiment of a dilation system of the present invention is comprised of a directional sequential dilation system 10. The directional sequential dilation system 10 preferably includes a stimulating probe 20, a first directional dilator 30 and a second directional dilator 40. The directional sequential dilation system 10 may include more or less dilators such as, for example, one, three, four, etc. The stimulating probe 20 can be any probe now or hereafter known for transmitting an electrical pulse. The stimulating probe 20 preferably includes a probe tip 20a and a longitudinal probe axis 21. The first directional dilator 30 preferably includes a first longitudinal axis 31, an outer surface 32, a proximal end 33, a distal end 34 and a first bore 35 extending from the proximal end 33 to the distal end 34. The first directional dilator 30 also preferably includes a first tip 30a at the distal end 34 through which the first longitudinal axis 31 extends. The first bore 35 has a first bore axis 36 that extends from a proximal end to a distal end of the first bore 35. The first longitudinal axis 36 is preferably offset or located a first offset distance A from the first longitudinal axis 31. The first directional dilator 30 also preferably includes a first channel 38 formed in the outer surface 32 thereof. The first channel 38 is preferably in communication with the first bore 35 along the entire length of the first bore 35. In use, the first bore 35 and the first channel 38 removably receive the stimulating probe 20 in an assembled configuration (e.g., when the stimulating probe 20 is slidably received within the first bore 35 of the first directional dilator 30) so that a surgeon can stimulate the first directional dilator 30. The probe axis 21 of the stimulating probe 20 is preferably coaxial with the first bore axis 36 of the first directional dilator 30 in the assembled configuration.

Similarly, the second directional dilator 40 preferably includes a second longitudinal axis 41, an outer surface 42, a proximal end 43, a distal end 44 and a second bore 45 extending from the proximal end 43 to the distal end 44. The second bore 45 preferably has a second bore axis 46 that extends from the proximal end 43 to the distal end 44. The second directional dilator 40 also preferably includes a second tip 40a at the distal end 44 through which the second longitudinal axis 41 extends. The second bore axis 46 of the second bore 45 is offset or located a second offset distance B from the second longitudinal axis 41. The outer surfaces 32, 42 of the first and second directional dilators 30, 40 are preferably coated to prevent electrical leakage during use, as will be apparent to one having ordinary skill in the art. The second directional dilator 40 also preferably includes a second channel 48 formed in the outer surface 42 thereof that is in communication with the second bore 45. In use, the second bore 45 and the second channel 48 receive the first directional dilator 30 therein in the assembled configuration (e.g., when the first directional dilator 30 is slidably received within the second bore 45 of the second directional dilator 40). The first longitudinal axis 31 of the first directional dilator 30 is preferably coaxial with the second bore axis 46 of the second directional dilator 40 when in the assembled configuration.

Because the first and second bore axes 36, 46 of the first and second bores 35, 45 are offset from the first and second longitudinal axes 31, 41 of the first and second directional dilators 30, 40, respectively, inserting the first directional dilator 30 over the stimulating probe 20 and then the second directional dilator 40 over the first directional dilator 30 causes each sequential dilator to "directionally" dilate the opening formed in the patient preferably away from any neural elements, nerves 9 or other anatomic structure on the opposite side of the stimulating probe 20, as will be described in greater detail below.

Moreover, incorporation of the first and second channels 38, 48 enables the first and second directional dilators 30, 40 to be more closely nested together and thus, substantially eliminate the "cookie cutter" effect that is realized when using multiple concentric dilators of increasing inner bore size.

The first directional dilator 30 preferably includes a plurality of first depth indicators 37 located on the outer surface 32 thereof (as best shown in FIGS. 5A and 5B). The plurality of first depth indicators 37 extend, on the outer surface 32 of the first directional dilator 30, generally perpendicular to the first longitudinal axis 31. The plurality of first depth indicators 37 indicate to the surgeon the various distances between the first tip 30a formed at the distal end 34 of the first directional dilator 30 to the respective depth indicator 37 so that, in use, the surgeon can determine how far the first directional dilator 30 has been inserted into the patient. Similarly, as best shown in FIGS. 6A and 6B, the second directional dilator 40 preferably includes a plurality of second depth indicators 47 located on the outer surface 42 thereof. The plurality of second depth indicators 47 extend, on the outer surface 42 of the second directional dilator 40, generally perpendicular to the second longitudinal axis 41. The plurality of second depth indicators 47 indicate to the surgeon the various distances between the second tip 40a formed at the distal end 44 of the second directional dilator 40 to the respective depth indicator 47 so that, in use, the surgeon can determine how far the second directional dilator 40 has been inserted into the patient. In the first preferred embodiment, the plurality of first and second depth indicators 37, 47 are spaced a distance of eighty millimeters (80 mm) to one hundred fifty millimeters (150 mm) from the first and second tips 30a, 40a in ten millimeter (10 mm) increments. However, the plurality of plurality of first and second depth indicators 37, 47 are not limited to these dimensions and may be spaced from the first and second tips 30a, 40a at nearly any distance or spacing that is preferred by a surgeon and is able to show the depth that the first and second directional dilators 30, 40 are inserted into the patient.

In addition, the first and second directional dilators, 30, 40 preferably include first and second grips 39, 49, respectively, located at the proximal ends 32, 42 thereof to better enable the surgeon to grip the dilators 30, 40 in use. The first and second grips 39, 49 may be utilized by the surgeon during insertion, removal, twisting or otherwise manipulating the first and second directional dilators 30, 40 during surgery.

As best shown in FIG. 1, the first directional dilator 30 preferably has a first length Li while the second directional dilator 40 has a second length L2. The first length Li is preferably greater than the second length L2 to facilitate handling and insertion. Similarly, the stimulating probe 20 preferably has a probe length L3 such that the probe length L3 is greater than the first length Li and the second length L2. The greater first length Li of the first directional dilator 30 permits the proximal end 33 of the first directional dilator 30 to extend further out of the patient in the assembled and operational configurations such that a surgeon may grasp the first grip 39 and remove or otherwise manipulate the first directional dilator 30 even after the second directional dilator 40 is inserted into the patient. In the first preferred embodiment, the first length is two hundred twenty millimeters (220 mm) and the second length is two hundred millimeters (200 mm), but are not so limited and may have nearly any length that permits insertion into the patient with the proximal ends 33, 43 extending out of the patient. In addition, the first directional dilator 30 preferably has a first diameter Di and the second directional dilator 40 has a second diameter D2, the second diameter D2 is preferably greater than the first diameter Dl. In the first preferred embodiment, the first diameter Di is approximately seven and seven tenths millimeters (7.7 mm) and the second diameter D2 is approximately seventeen and one-half millimeters (17.5 mm). However, the first and second diameters Di, D2 are not so limited and may have nearly any diameter desired by the surgeon for dilating tissue various distances from the stimulating probe 20. Further, the first and second directional dilators 30, 40 are not limited to having a circular cross-section and may have nearly any cross-section and be adapted to shapes that permits directional dilation in a manner that is preferred by a surgeon. For example, the first and second directional dilators 30, 40 may have an oval or oblong cross-sectional shape that urges dilation and a surgical working channel even further from a detected nerve 9 than a dilator having a circular cross-section.

A method of using the stimulating probe 20 and first and second directional dilators 30, 40 will now be described for accessing the patient's spine 2. The technique may be particularly desirable for accessing the lumbar region of the spine 2 via a lateral approach, although a similar or the same method may be used in other parts of the patient's body.

Using the stimulating probe 20 and a triggered electromyograph (EMG) 50, the surgeon preferably maps a safe zone, i.e., a zone generally free of any neural elements or nerves 9, on the tissue of interest (e.g., psoas muscle 4). For example, on the psoas muscle 4, the anterior third of the psoas muscle 4 is generally considered a safe zone.

Once a safe zone is established, anatomical placement is preferably confirmed via intra-operative fluoroscopy. The surgeon inserts the stimulating probe 20 through the psoas muscle 4 toward the patient's spine 2. If the surgery is being performed on the intervertebral disc space 6, the distal end of the stimulating probe 20 may be inserted into the annulus of the desired intervertebral disc space 6. Preferably, the stimulating probe 20 will be inserted via the most posterior portion of the safe zone.

The surgeon can insert or slide the first directional dilator 30 over the stimulating probe 20 so that the first longitudinal axis 31 is located to one side of the stimulating probe 20, preferably away from a sensed neural element or nerve 9, through the psoas muscle 4 and into a position proximate the patient's spine 2. The surgeon can then insert the second directional dilator 40, if necessary, to further dilate the tissue proximate the outside surface 32 of the first directional dilator 30 and further away from the sensed neural element or nerve 9. The surgeon can repeat this process as often as necessary. Finally, if desired, a retractor 60 can be inserted over the second directional dilator 40 to subsequently retract the tissue and to permit removal of the first and second directional dilators 30, 40 and the stimulating probe 20. Alternatively, a working cannula (not shown) may be inserted over the second dilator 40 such that a procedure on the spine 2 may be performed through the working cannula.

Additionally, if desired, before inserting the second directional dilator 40, the stimulating probe 20 can be removed from the first bore 35 and the dilator/probe combination rotated. Thereafter, using the triggered EMG stimulation 50, the surgeon can verify that the nerve root 9 is located at the expected side of the first directional dilator 30, preferably opposite the first channel 38. The stimulating probe 20 is preferably re-inserted into the first bore 35, before insertion of the second directional dilator 40.

By using the first and second directional dilators 30, 40, as compared to concentric sequential dilators as are generally known to those having skill in the art, the directional sequential dilation system 10 preferably ensures that the access opening is created away from the neural elements or nerves 9 of the psoas muscle 4, thus avoiding any neural elements or nerves 9 that may, for example, be located on the posterior side of the stimulating probe 20.

Moreover, the directional sequential dilation system 10 also reduces the amount of tissue damage when separating the tissue by minimizing the amount of tissue separation.

Alternatively, as shown in FIGS. 7-10, a one step blunt stimulating dilator 100 comprising a second preferred embodiment of a dilation system of the present application may be used. The blunt stimulating dilator 100 includes an outer surface 102, a proximal end 104, a distal end 106 and a bore 108 extending from the proximal end 104 to the distal end 106. The proximal end 104 includes an area 110 for attaching a stimulating clip or cord. The distal end 106 includes an exposed, preferably pointed tip 112 for delivering electrical stimulation. The outer surface 102 of the stimulating dilator 100 between the proximal and distal ends 104, 106 is preferably coated to prevent electrical leakage. The stimulating dilator 100 also preferably includes a channel 114 formed in the outer surface 102 thereof for receiving a stimulating probe, such as the stimulating probe 20 illustrated in FIG. 1. The stimulating probe can be any probe now or hereafter known for transmitting an electrical pulse.

The stimulating dilator 100 offers the surgeon the ability to simultaneously stimulate and dilate the psoas muscle 4. After placing the tip 112 of the stimulating dilator 100 into the disc space, the stimulating probe 20 can be inserted through the channel 114 along the outer surface 102 of the dilator 100 to stimulate the periphery of the dilated tissue.

Figure 11:
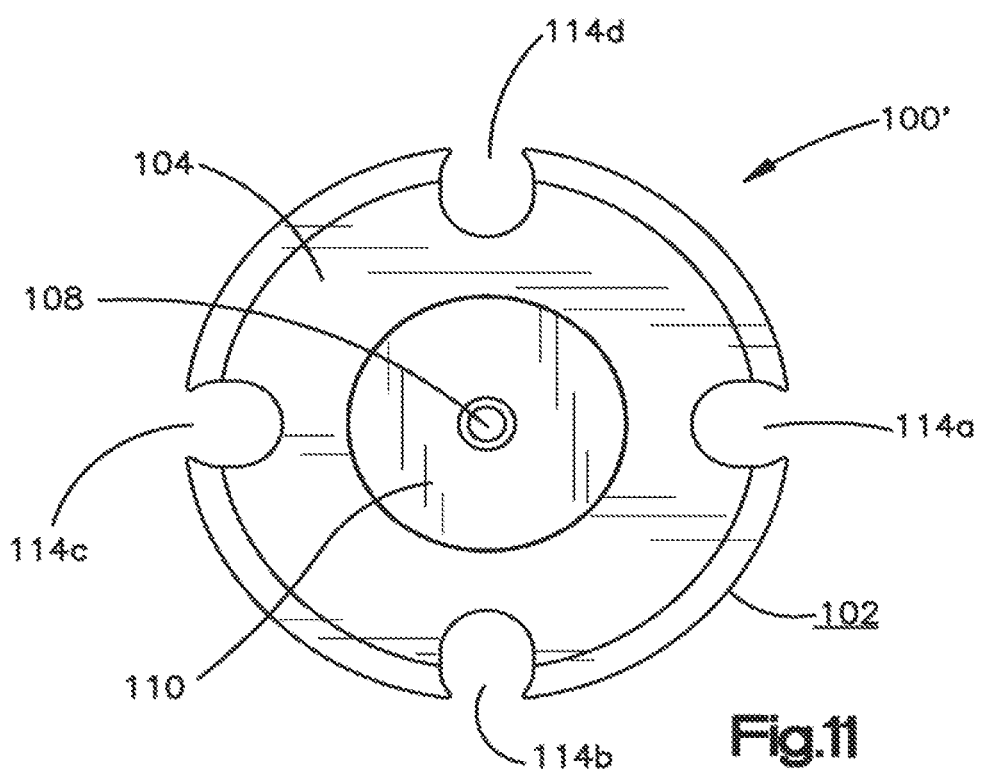
FIG. 11 illustrates a top plan view of a dilation system in accordance with a third preferred embodiment of the present invention, which is also comprised of a blunt stimulating dilation system.
Figure 12:
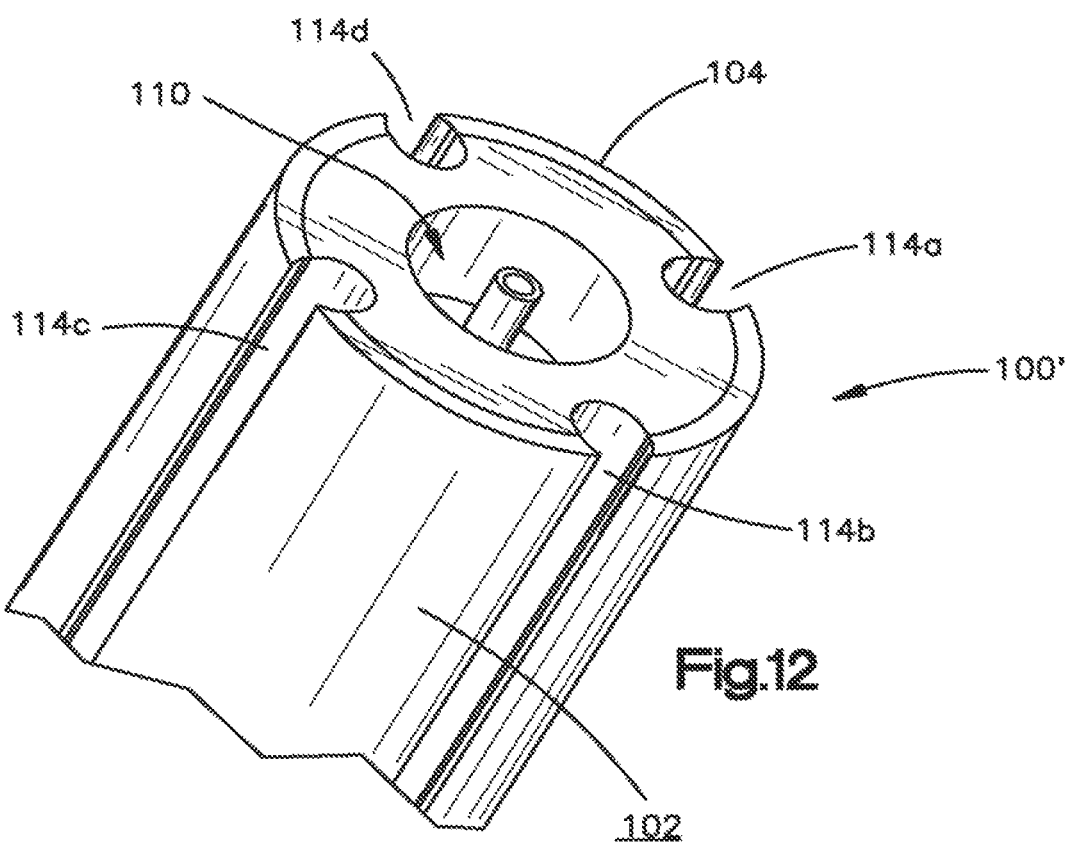
FIG. 12 illustrates a magnified, top perspective view of a proximal end of the blunt stimulating dilation system of FIG. 11.

Alternatively, as shown in FIGS. 11 and 12, the stimulating dilator 100' comprised of a third preferred embodiment of the present application may include a plurality of channels 114 formed in the outer surface 102 thereof. For example, as shown, the stimulating dilator 100' may include four channels 114a-d diametrically spaced on the outer surface 102 of the dilator 100'. In this manner, the surgeon can stimulate anterior, posterior, cranially, and caudally to verify the location of the nerve root once the dilator 100' is in place. Although as will be understood by one of ordinary skill in the art, the stimulating dilator 100' may include any number of channels 114 including, for example, two, three, five or more.

A method of using the blunt stimulating dilation system will now be described to produce access to the spine 2, in particular to provide an access opening through the psoas muscle 4 in the lumbar region of the spine 2 via a lateral approach. Although as will be understood by one of ordinary skill in the art, the method may be used in other parts of the body and utilizing alternative approaches.

In use, a surgeon inserts, preferably laterally, the blunt stimulating dilator 100, 100' into the psoas 4 muscle via, for example, a twisting motion. The surgeon preferably uses a triggered EMG 50 to transmit an electrical pulse into the blunt stimulating dilator 100, 100' in order to locate a safe zone in the patient's psoas muscle 4 by locating nerve roots 9. Once the location of any nerve root 9 has been confirmed to be posterior to the blunt stimulating dilator 100, 100', the surgeon can laterally insert the blunt stimulating dilator 100, 100' through the psoas muscle 4 and toward the patient's spine 2, preferably into the annulus of the disc space 6. The surgeon inserts or slides the stimulating probe 20 into the channel 114 formed in the outer surface 102 of the blunt stimulating dilator 100, 100'. If desired, the surgeon rotates the blunt stimulating dilator 100 with the stimulating probe 20 located in the channel 114 while using the EMG 50 to verify the location of the nerve root 9. Alternatively, in connection with the four channel blunt stimulating dilator 100', rotation of the blunt stimulating dilator 100 is not required. Rather, the stimulating probe 20 can be independently inserted into each channel 114a-d to verify the location of the nerve root 9. The surgeon can then, if desired, insert a retractor over the stimulating dilator 100, 100'.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A method of forming an access opening through a psoas muscle to a patient's spine, comprising:
    (a) inserting a stimulating probe into the psoas muscle to locate a nerve and a safe zone in the psoas muscle, the stimulating probe having a probe axis and a probe tip;
    (b) inserting the stimulating probe through the psoas muscle so the probe tip is proximate the patient's spine;
    (c) obtaining a first directional dilator having a longitudinal axis, a bore with a length extending from a proximal end to a distal end, a bore axis that is offset from the longitudinal axis, and a channel formed in an outer surface thereof and extending from the proximal end to the distal end so as to be in communication with the bore along an entirety of the length of the bore;
    (d) inserting the first directional dilator through the psoas muscle and toward the patient's spine guided by sliding engagement of the stimulating probe with the bore of the first directional dilator and with the channel of the first directional dilator positioned between the nerve and the longitudinal axis of the first directional dilator;
    (e) obtaining a second directional dilator having a longitudinal axis, a bore with a length extending from a proximal end to a distal end, a bore axis that is offset from the longitudinal axis, and a channel formed in an outer surface thereof and extending from the proximal end to the distal end so as to be in communication with the bore along an entirety of the length of the bore; and
    (f) inserting the second directional dilator through the psoas muscle toward the patient's spine guided by sliding engagement of the first directional dilator with the bore of the second directional dilator and with the channel of the second directional dilator positioned between the nerve and the longitudinal axis of the second directional dilator.

2. The method of claim 1, wherein in the step of inserting the first directional dilator, the bore axis of the first directional dilator is coaxial with the probe axis.

3. The method of claim 1, wherein in the step of inserting the second directional dilator, the bore axis of the second directional dilator is coaxial with the longitudinal axis of the first directional dilator.

4. The method of claim 1, wherein the first directional dilator has a first length and the second directional dilator has a second length, and wherein the first length is greater than the second length so the first directional dilator extends beyond the second directional dilator upon the second directional dilator being inserted through the psoas muscle.

5. The method of claim 4, wherein the stimulating probe has a probe length that is greater than the first length so the stimulating probe extends beyond the first directional dilator upon the first directional dilator being inserted through the psoas muscle.

6. The method of claim 1, wherein the channel of the first directional dilator is radially aligned with the channel of the second directional dilator when the stimulating probe is received in the bore of the first directional dilator and when the first directional dilator is received in the bore of the second directional dilator.

7. The method of claim 1, further comprising the step of: inserting a retractor over the second directional dilator.

8. The method of claim 1, further comprising the step of: confirming via intra-operative fluoroscopy the location of the safe zone prior to step (b).

9. A method of forming an access opening through a psoas muscle to a patient's spine, comprising:
   (a) inserting a stimulating probe into the psoas muscle to locate a nerve and a safe zone in the psoas muscle, the stimulating probe having a probe axis and a probe tip;
   (b) inserting the stimulating probe through the psoas muscle so the probe tip is proximate the patient's spine;
   (c) obtaining a first directional dilator having a longitudinal axis, a bore with a length extending from a proximal end to a distal end, a bore axis that is offset from the longitudinal axis, and a channel formed in an outer surface thereof and extending from the proximal end to the distal end so as to be in communication with the bore along at least a portion of the length of the bore;
   (d) inserting the first directional dilator through the psoas muscle and toward the patient's spine guided by sliding engagement of the stimulating probe with the bore of the first directional dilator and with the channel of the first directional dilator positioned between the nerve and the longitudinal axis of the first directional dilator;
   (e) obtaining a second directional dilator having a longitudinal axis, a bore with a length extending from a proximal end to a distal end, a bore axis that is offset from the longitudinal axis of the second directional dilator, and a channel formed in an outer surface thereof and extending from the proximal end to the distal end so as to be in communication with the bore of the second directional dilator along at least a portion of the length of the bore of the second directional dilator; and
   (f) inserting the second directional dilator through the psoas muscle toward the patient's pine guided by sliding engagement of the first directional dilator with the bore of the second directional dilator and with the channel of the second directional dilator positioned between the nerve and the longitudinal axis of the second directional dilator.

10. The method of claim 9, wherein in the step of inserting the first directional dilator, the bore axis of the first directional dilator is coaxial with the probe axis.

11. The method of claim 9, wherein in the step of inserting the second directional dilator, the bore axis of the second directional dilator is coaxial with the longitudinal axis of the first directional dilator.

12. The method of claim 9, wherein the first directional dilator has a first length and the second directional dilator has a second length, and wherein the first length is greater than the second length so the first directional dilator extends beyond the second directional dilator upon the second directional dilator being inserted through the psoas muscle.

13. The method of claim 12, wherein the stimulating probe has a probe length that is greater than the first length so the stimulating probe extends beyond the first directional dilator upon the first directional dilator being inserted through the psoas muscle.

14. The method of claim 9, wherein the channel of the first directional dilator is radially aligned with the channel of the second directional dilator when the stimulating probe is received in the bore of the first directional dilator and when the first directional dilator is received in the bore of the second directional dilator.

15. The method of claim 9, further comprising the step of: inserting a retractor over the second directional dilator.

16. The method of claim 9, further comprising the step of: confirming via intra-operative fluoroscopy the location of the safe zone prior to step (b).

* * * * *